(12) United States Patent
Heemskerk et al.

(10) Patent No.: US 7,588,913 B2
(45) Date of Patent: Sep. 15, 2009

(54) PROCESS FOR THE PREPARATION OF CEPHRADINE

(75) Inventors: Dennis Heemskerk, Schinveld (NL); Anja Gerarda Margaretha Hogenboom, Maria Hoop (NL); Carlos Enrique Lenhardt, Alella Barcelona (ES); Harold Monro Moody, Gulpen (NL); Theodorus Johannes Godfried Maria Van Dooren, Roermond (NL)

(73) Assignee: DSM IP Assets B.V., Heerlen (NL)

( * ) Notice: Subject to any disclaimer, the term of this patent is extended or adjusted under 35 U.S.C. 154(b) by 399 days.

(21) Appl. No.: 10/562,345

(22) PCT Filed: Jul. 1, 2004

(86) PCT No.: PCT/EP2004/007291

§ 371 (c)(1),
(2), (4) Date: Feb. 7, 2006

(87) PCT Pub. No.: WO2005/003367

PCT Pub. Date: Jan. 13, 2005

(65) Prior Publication Data

US 2006/0189802 A1  Aug. 24, 2006

(30) Foreign Application Priority Data

Jul. 3, 2003 (EP) ................. 03077102
Nov. 28, 2003 (EP) ................. 03104445

(51) Int. Cl.
C12P 35/04 (2006.01)
C07D 501/22 (2006.01)

(52) U.S. Cl. ......................... 435/50; 540/230

(58) Field of Classification Search ................. 540/230; 435/50

See application file for complete search history.

(56) References Cited

U.S. PATENT DOCUMENTS

| | | | |
|---|---|---|---|
| 3,485,819 A | 12/1969 | Weisenborn | |
| 3,819,620 A | 6/1974 | Dursch et al. | |
| 4,073,687 A | 2/1978 | Kondo et al. | |
| 4,139,702 A * | 2/1979 | Broggi et al. | 540/227 |
| 5,034,522 A | 7/1991 | Schreiber | |
| 5,278,157 A * | 1/1994 | Meseguer et al. | 514/209 |
| 2005/0124029 A1* | 6/2005 | Alkema et al. | 435/50 |

FOREIGN PATENT DOCUMENTS

| | | |
|---|---|---|
| EP | 0 997 199 | 5/2000 |
| WO | WO 91/00865 | 1/1991 |
| WO | WO 96/02663 | 2/1996 |
| WO | WO 97/04086 | 2/1997 |
| WO | WO 98/56944 | 12/1998 |
| WO | WO 99/24441 | 5/1999 |
| WO | WO 99/31109 | 6/1999 |
| WO | WO 03/055892 | 7/2003 |
| WO | WO 03/055998 | 7/2003 |

OTHER PUBLICATIONS

K. Florey, Analytical Profiles of Drug Substances, vol. 5, pp. 21-59 (1976).*
International Search Report, (2006).

* cited by examiner

Primary Examiner—Mark L Berch
(74) Attorney, Agent, or Firm—Nixon & Vanderhye, P.C.

(57) ABSTRACT

The present invention describes a process for preparing cephradine, said process comprising reacting 7-aminodesacetoxy cephalosporanic acid (7-ADCA) with D-dihydrophenylglycine in activated form (DHa) in the presence of an enzyme in a reaction mixture to form cephradine, resulting in a conversion of 7-ADCA into cephradine of at least 70%, wherein the concentration D-dihydrophenylglycine (DH) in the reaction mixture is below 2 wt.%, wherein the conversion of 7-ADCA into cephradine & equals; $(n_{CEF}/n_{7-ADCA})*100\%$, wherein $n_{CEF}$=quantity of cephradine formed (in mole); and $n_{7-ADCA}$=total quantity of 7-ADCA added to reaction mixture (in mole). The invention also describes a process for the preparation of cephradine hydrate characterised in that the process comprises: —reacting 7-amino acid desacetoxy cephalosporanic acid (7-ADCA) with DHa in the presence of an enzyme in a reaction mixture to form cephradine; —preparing an aqueous solution comprising at least part of the cephradine; and crystallising the cephradine from said aqueous solution. The invention further describes cephradine hydrate obtainable by a process according to invention. The invention also describes cephradine hydrate with an absorbance at 450 nm of below 0.050.

23 Claims, No Drawings

PROCESS FOR THE PREPARATION OF CEPHRADINE

This application is the U.S. national phase of international application PCT/EP2004/007291 filed 1 Jul. 2004 which designated the U.S. and claims benefit of EP 03077102.6, dated 3 Jul. 2003 and EP 0310445.6, dated 28 Nov. 2003, the entire content of which is hereby incorporated by reference.

The present invention relates to a process for the preparation of cephradine which comprises reacting 7-aminodesacetoxy cephalosporanic acid (7-ADCA) with D-dihydrophenylglycine in activated form (DHa) in the presence of an enzyme, and cephradine obtainable by the process according to the invention.

WO-A-97/04086 discloses the enzymatic production of β-lactam antibiotics by reaction of a parent β-lactam with a side chain in activated form, including the preparation of cephradine by reaction of 7-aminodesacetoxy cephalosporanic acid (7-ADCA) with D-dihydrophenylglycine in activated form (DHa). This publication describes that besides the synthesis reaction, i.e. the reaction of the activated side chain with the parent β-lactam, also side chain acids are formed by hydrolysis of the activated side chain and the desired product. The side chain acid formed in case of the enzymatic production of cephradine is D-dihydrophenylglycine (DH). WO 97/04086 discloses inter alia the enzymatic synthesis of cephradine in the presence of wild-type acylase of *E. coli*, and shows that when penicillin acylase was immobilised on a specific carrier, an increased synthesis/hydrolysis (S/H) ratio was obtained.

In the process of WO 97/04086 conversions of 7-ADCA and dihydrophenylglycine methyl ester into cephradine of up to 68% had been achieved.

It was found that when looking for methods for the enzymatic synthesis of cephradine resulting in increased conversions, significant processibility problems are encountered. In particular, it was found that the reaction mixture may become highly viscous when increasing the conversion, and that said increased viscosity can even preclude working at higher conversions in a practical manner.

An object of the present invention is to be able to work at high conversions of 7-ADCA and DHa into cephradine.

This object is achieved according to the invention by providing a process for preparing cephradine, said process comprising reacting 7-aminodesacetoxy cephalosporanic acid (7-ADCA) with D-dihydrophenylglycine in activated form (DHa) in the presence of an enzyme in a reaction mixture to form cephradine, resulting in a conversion of 7-ADCA into cephradine of at least 70%, wherein the concentration D-dihydrophenylglycine (DH) in the reaction mixture is below 2 wt. %.

Surprisingly it was found that the viscous mixture is the result of crystallisation of hydrolysis product that is formed during the reaction, i.e. DH. By maintaining the concentration DH low according to the invention, crystallisation of DH can be minimised or avoided, and increased conversions can be achieved without processibility problems. A further advantage of the process according to the invention is that recovery of cephradine from the reaction mixture can be effected in a simple way, resulting in a stable and high quality product.

As used herein 7-aminodesacetoxy cephalosporanic acid will also be referred to as 7-ADCA.

As used herein D-dihydrophenylglycine in activated form will also be referred to as DHa.

As used herein D-dihydrophenylglycine will also be referred to as DH.

The process according to the invention comprises reacting 7-aminodesacetoxy cephalosporanic acid (7-ADCA) with D-dihydrophenylglycine in activated form (DHa) in the presence of an enzyme in a reaction mixture to form cephradine, resulting in a conversion of 7-ADCA into cephradine of at least 70%, preferably at least 80%, more preferably at least 90%. As used herein the conversion of 7-ADCA into cephradine is defined as $(n_{CEF}/n_{7-ADCA})*100\%$, wherein $N_{CEF}$=total quantity of cephradine formed (in mole); and
$n_{7-ADCA}$=total quantity of 7-ADCA added to the reaction mixture (in mole).

The cephradine formed may be present in the reaction mixture in any form, e.g. in dissolved form and/or in solid form, e.g. as cephradine hydrate.

The 7-ADCA may be added to the reaction mixture in any suitable way. It is possible to add the total quantity of 7-ADCA to the reaction mixture at once. It is also possible to add at least part of the 7-ADCA to the reaction mixture during the course of the reaction.

According to the invention, the concentration of DH in the reaction mixture is below 2 wt. %. Preferably, the concentration of DH in the reaction mixture is below 1.5 wt.%, more preferably below 1.0 wt.%, more preferably below 0.8 wt. %. Decreased concentrations of DH in the reaction mixture have the advantage that the formation of a viscous mixture due to crystallisation of DH is further reduced or completely avoided. As used herein, the concentration of DH expressed as wt. % is given relative to the total weight of the reaction mixture, i.e. the total weight including the weight of the liquid phase and the weight of solid components that may be present in the reaction mixture, for instance immobilised enzyme and/or solid reactant or reaction products.

The reaction mixture may be any suitable mixture in which the reaction of 7-ADCA with DH in activated form may be carried out in the presence of an enzyme. Preferably, the reaction mixture is an aqueous reaction mixture. The aqueous reaction mixture may also contain an organic solvent or a mixture of organic solvents, preferably less than 30 vol.%, more preferably less than 20 vol.%, more preferably less than 10 vol.%, more preferably less than 5 vol.% (relative to the total volume of the liquid). Preferably, the organic solvent is an alcohol with 1-7 carbon atoms, for instance a monoalcohol, in particular methanol or ethanol; a diol, in particular ethylene glycol, or a triol, in particular glycerol. Preferably, the aqueous reaction mixture contains at least 70 vol.% water, more preferably at least 80 vol.%, more preferably at least 90 vol.%, most preferably at least 95 vol.% water (relative to the sum volume of the liquid).

In the process according to the invention DHa may be an amide, for instance a primary, secondary or tertiary amide, or an ester of D-dihydrophenylglycine (DH). Preferably, DHa is an ester of DH, for instance a lower alkyl (1-4 C) ester of DH. Preferred is D-dihydrophenylglycine methyl ester (DHMe), and most preferred DHMe in the form of a salt, for example a formic acid or HCl salt of DHMe. The formic acid or HCl salt of other DH esters may also be used.

The concentration DH in the reaction mixture can be maintained below 2 wt.%, throughout the reaction preferably below 1.5 wt.%, preferably below 1 wt.%, more preferably below 0.8 wt.% in any suitable way. Preferred conditions are disclosed below.

The molar ratio of DHa to 7-ADCA, i.e. the total quantity of DHa added to the reaction mixture divided by the total quantity of 7-ADCA added to the reaction mixture, both expressed in moles, may vary between wide limits. Preferably, the molar ratio is below 2.5, preferably between 0.5 and 2.0, and more preferably between 0.7 and 1.8.

The concentrations of 7-ADCA and DH in activated form (DHa) applied in the reaction mixture may vary between wide limits. The sum of the molar quantity of 7-ADCA added to the reaction mixture and DHa added to the reaction mixture may be between 10 and 2000 mmole per liter of reaction mixture, preferably between 50 and 1500 mmole per liter of reaction mixture.

In a preferred embodiment of the present invention reacting 7-ADCA with DHa results in a conversion of DHa into cephradine of at least 70%, preferably at least 80%, more preferably at least 90%, wherein conversion of DHa into CEF=$(n_{CEF}/n_{DHa})$*100%, wherein $n_{CEF}$=total quantity of cephradine formed (in mole); and $n_{DHa}$=total quantity of DHa added to reaction mixture (in mole).

The DHa in the reaction mixture may be added in many ways. All the DHa may be added, initially, i.e. at the start of the reaction, for instance in a batch process. It is also possible to add at least part of the DHa to the reaction mixture during the course of the reaction.

The concentration OH in the reaction mixture may be maintained below 2 wt.% throughout the reaction, preferably below 1.5 wt.%, preferably below 1 wt.%, more preferably below 0.8 wt.%, e.g. by controlling the pH of the reaction mixture and/or the temperature.

The pH and temperature applied may vary between wide ranges. The reaction to form the cephradine may for instance be carried out at a temperature of between −5 and 35° C., preferably between 0 and 30° C. More preferably, the reaction is carried out at a temperature of between 5° C. and 25° C.

The reaction to form the cephradine may for instance be carried out at a pH of between 6 and 9. Preferably, the reaction is carried out at a pH of between 6.3 and 8.5.

The pH of the reaction mixture may be adjusted at the desired pH value in several ways, for instance chemically by adding an acid, for instance a mineral acid, in particular sulphuric acid, hydrochloric acid or nitric acid. The pH may also be adjusted at the desired pH value by adding a base, for instance sodium hydroxide or ammonia.

The concentration DH in the reaction mixture may also be maintained below 2 wt.% throughout the reaction, preferably below 1.5 wt.%, preferably below 1 wt.%, more preferably below 0.8 wt.% by working at diluted concentrations of the reactants 7-ADCA and DHa or by using an enzyme with improved properties, for instance an improved S/H-ratio, which may be a wild type or mutant enzyme. Maintaining the concentration of DH low according to the invention allows the conversion to be increased. This can then for instance be achieved by applying a residence time that is sufficiently long.

Any enzyme may be used that is suitable as a catalyst in reacting 7-ADCA with DH in activated form to prepare cephradine in the process according to the invention. Such enzymes are for instance the enzymes that are known under the general term penicillin acylase, or penicillin G acylase, also called penicillin G amidase or benzylpenicillin acylase (EC 3.5.1.11). Penicillin G acylase refers to a group of hydrolases from microorganisms, especially bacteria, capable of hydrolyzing the 6-acyl group of penicillins or the 7-acyl group of cephalosporins. Penicillin acylase enzymes may be classified both on the basis of their substrate specificity and on the basis of their molecular structure, which is described in various publications, see for instance WO 03/055998 and WO 98/20120.

Microorganisms from which penicillin acylase enzymes may be obtained are for example *Acetobacter*, in particular *Acetobacter pasteurianum, Aeromonas, Alcaligenes*, in particular *Alcaligenes faecalis, Aphanocladium, Bacillus* sp., in particular *Bacillus megaterium, Cephalosporium, Escherichia*, in particular *Escherichia coli, Flavobacterium, Fusarium*, in particular *Fusarium oxysporum* and *Fusarium solani, Kluyvera, Mycoplana, Protaminobacter, Proteus*, in particular *Proteus rettgari, Pseudomonas* and *Xanthomonas*, in particular *Xanthomonas citril*.

In one embodiment of the invention the enzyme may be immobilised on a carrier. In immobilised form the enzyme can be readily separated and recycled. Immobilised enzymes are known as such and are commercially available, for example an *E coli* penicillin acylase isolated as decribed in WO 92/12782 and immobilised as described in EP 222 462 and in WO 97/04086.

The process for preparing cephradine according to the invention may be carried out at any suitable pH and temperature, for instance depending on the enzyme used. For instance, the process comprising reacting 7-ADCA with DHa to form cephradine may be carried out in the presence of a wild type penicillin acylase and at a temperature below 15° C. Preferably, the process comprising reacting 7-ADCA with DHa to form cephradine in the presence of a wild type penicillin acylase is carried out at a temperature below 15° C. and at a pH of at least 7.0.

Applicant found that for enzymes having an increased S/H ratio with respect to the wild-type acylase of *E. coli*, increased conversions are achieved if the reaction is carried out at relatively high temperature, e.g. above 15° C., preferably between 15 and 30° C. and relatively low pH, e.g. below 7.7, preferably between 6 and 7.5. Therefore the invention also relates to a process comprising reacting 7-ADCA with DHa to form cephradine which is carried out in the presence of an enzyme being an acylase having a higher S/H ratio preferably a higher $S/H_{ini}$ than the wild-type acylase of *E.coli* and at a temperature of at least 15° C., preferably between 15 and 30° C. Preferably, reacting 7-ADCA with DHa to form cephradine in the presence of an enzyme being an acylase having a higher S/H ratio than the wild-type acylase of *E.coli* is carried out at a temperature of at least 15° C., preferably between 15 and 30° C. and at a pH of below 7.7, preferably between 6 and 7.5.

This is surprising as in the case of the enzyme having a relatively low S/H ratio, the highest conversions were found to be achieved at relatively low temperature and relatively high pH. The above effect is in particular pronounced when the acylase having an increased S/H ratio has a lower enzymatic activity than that of the wild-type acylase of *E. coli*.

The acylase having a higher S/H ratio than the wild-type acylase of *E. coli*, may be any enzyme. The enzyme may for example be a mutant penicillin acylase. Mutants of penicillin acylases or acylase mutants, can be made by starting from any known penicillin acylase. Mutated acylases are for example derived from wild-type acylases via recombinant DNA methodology known in the art, by substituting one amino acid residue for a new residue.

In a preferred embodiment of the present invention the enzyme is a mutant penicillin acylase having an amino acid substitution at the position 24 of the β-subunit corresponding to the β-subunit of penicillin acylase of *E.coli*. In a preferred embodiment, the L-phenylalanine at the position 24 of the β-subunit corresponding to the β-subunit of penicillin acylase of *E.coli*, has been replaced in that position by L-alanine, as is described in WO 98/20210. This mutation can be applied on a Pen G acylase from *E. coli*, but Pen G acylases from other sources may also by used. The numbering of the position of the amino acids corresponds to the numbering of the amino acid sequence of wild type Penicillin G acylase of *E. coli*.

As defined herein, the synthesis/hydrolysis (S/H) ratio is understood to be the molar ratio of synthesis product to hydrolysis product at a particular moment during the enzymatic reaction. Synthesis product is understood to be the β-lactam antibiotic formed from the activated side chain and β-lactam nucleus. Hydrolysis product is understood to be the corresponding acid of the activated side chain.

The S/H ratio is a function of the concentration of the reactants, the molar ratio of activated side chain to β-lactam nucleus, the temperature, the pH and the enzyme. In the ideal situation a comparative experiment is carried out where the particular candidate is tested against a reference enzyme, preferably E.coli PenG acylase, under the same conditions.

During an enzymatic acylation reaction the S/H ratio generally decreases. The S/H ratio of different penicillin acylases are preferably compared at equal conversion. They are most usually compared at 0% conversion (hence, at time t=0), the so-called initial S/H ratio ($S/H_{ini}$), which thus is a measure of the S/H ratio. The $S/H_{ini}$ can be determined with sufficient accuracy by carrying out the acylation reaction until a sufficiently high conversion is reached so that the products, in particular the hydrolysis product, can be measured accurately and then constructing a graph of $S/H_{ini}$ versus conversion and extrapolating it to 0% conversion. It might be necessary to determine the initial S/H ratio through extrapolation, since too little hydrolysis product is formed at low conversion for accurate determination of $S/H_{ini}$. Curve fitting algorithms which are known in the art may be applied to get a more reliable extrapolation. For accurate determination it is necessary to have sufficient data points. Sufficient data points means at least three data points, which should represent a difference in conversion of at least 0.5%.

Enzymatic activity can generally be defined as the molar quantity of reactant or product that is converted or synthesised per unit of time and per quantity of dissolved or immobilised enzyme at a particular moment during the enzymatic acylation reaction. Preferably, enzymes are applied in immobilised form and the enzymatic activity is defined per quantity of immobilised enzyme. The enzymatic activity per quantity of enzyme often is also indicated as specific activity of the particular enzyme.

The process according to the invention may be carried out in several ways, for instance in batch or continuous culture. Preferably, the process according to the invention is carried out in a batch process. A batch culture may be a batch culture, a fed-batch culture, a combination of batch and fed-batch mode, repeated fed-batch mode or any other combination.

The cephradine formed by the process according to the invention may be crystallised in any suitable manner.

Cephradine hydrate having an increased stability is preferably obtained according to the preferred embodiments described hereinafter.

Preferably, the process according to the invention comprises crystallising the cephradine from an aqueous solution. The aqueous solution may contain an organic solvent or a mixture of organic solvents, preferably less than 30 vol %, more preferably less than 20 vol.%, more preferably less than 10 vol.%, more preferably less than 5 vol.% (relative to the total volume of the liquid). Preferably, the organic solvent is an alcohol with 1-7 carbon atoms, for instance a monoalcohol, in particular methanol or ethanol; a diol, in particular ethylene glycol, or a triol, in particular glycerol. Preferably, the aqueous solution contains at least 70 vol.% water, more preferably at least 80 vol.%, more preferably at least 90 vol.%, most preferably at least 95 vol.% water (relative to the sum volume of the liquid).

The aqueous solution may contain 7-ADCA and/or DH.

The cephradine may be crystallised in any suitable form, typically in the form of cephradine hydrate. The invention is not limited to a specific cephradine hydrate. Typically, the cephradine hydrate is cephradine monohydrate. The water content of the cephradine hydrate may for instance range between 3% and 6% per weight.

Preferably, cephradine is crystallised from an aqueous solution wherein the ratio $m_{CEF}/(m_{7-ADCA}+m_{CEF})>0.7$, preferably>0.8, more preferably>0.9, and wherein $X_{DH}$ is between 0 and 2 wt.%, preferably between 0 and 1 wt.%, wherein $m_{CEF}$=molar quantity of cephradine in the aqueous solution;

$m_{7-ADCA}$=molar quantity of 7-ADCA in the aqueous solution; and $X_{DH}$=concentration of DH in the aqueous solution relative to the total weight of the aqueous solution. The total weight of the aqueous solution includes the weight of the liquid phase and the weight of any solid components present in the aqueous solution, for instance cephradine hydrate.

It was found that the preferred aqueous solution can efficiently be obtained by the process according to the invention resulting in increased conversions and low concentrations DH.

Crystallising cephradine from the preferred aqueous solution was found to result in an improved quality of the crystallised cephradine.

Therefore, the invention also relates to a process comprising reacting 7-aminodesacetoxy cephalosporanic acid (7-ADCA) with D-dihydrophenylglycine in activated form (DHa) in the presence of an enzyme in a reaction mixture to form cephradine; and crystallising the cephradine from an aqueous solution, in which aqueous solution the ratio $m_{CEF}/(m_{7-ADCA}+m_{CEF})>0.7$, preferably >0.8, more preferably>0.9, and wherein $X_{DH}$ is between 0 and 2 wt.%, preferably between 0 and 1 wt. %.

Preferably, the concentration of 7-ADCA in the aqueous solution is between 0 and 5 wt.%, preferably between 0 and 2 wt.% of the total weight of the aqueous solution. This was found to result in a further improvement of the quality of the crystallised cephradine.

The aqueous solution comprising the cephradine may be prepared in any suitable way.

Preferably, the process for preparing cephradine according to the Invention comprises separating the enzyme from the cephradine prior to said crystallising. The enzyme may for example be separated from the reaction mixture comprising the cephradine, for instance by sieving the reaction mixture over a sieve to separate the enzyme from the cephradine. In the reaction mixture part of the cephradine may be present in the form of cephradine hydrate, and the process may comprise dissolving the cephradine hydrate, and separating the enzyme from the resulting solution. Separating the enzyme from an aqueous solution comprising dissolved cephradine may for example be performed according to any suitable method, such as filtration or centrifugation.

In an embodiment of the process according to the invention part of the cephradine formed is present in the reaction mixture as cephradine hydrate, and the process further comprises dissolving at least part of said cephradine hydrate.

Cephradine hydrate may be dissolved in any suitable way. Dissolving cephradine hydrate may for example be performed at a pH at or above 8, more preferably, at a pH of between 8.3 and 9.5, and most preferably at a pH of between 8.5 and 9. In a preferred embodiment, dissolving cephradine hydrate is for example performed by modifying, in particular by increasing the pH of the reaction mixture to a value at or above 8, preferably, at a pH of between 8.3 and 9.5, and most preferably at a pH of between 8.5 and 9. The pH of the reaction mixture may be increased at the desired pH value by adding a suitable base, for example sodium hydroxide or ammonia. Said dissolving may be carried out batch-wise or continuously. It is also possible to separate cephradine hydrate from the reaction mixture, and to dissolve the separated cephradine hydrate to form the aqueous solution.

Crystallising cephradine from an aqueous solution comprising cephradine may be carried out at any suitable temperature. Surprisingly we found that improved product quality is achieved when the crystallisation is effected at increased temperature. The cephradine crystallised at these temperatures may have been prepared chemically or enzymatically.

Accordingly, the invention also relates to a process for preparing cephradine crystals, characterised in that the process comprises crystallising cephradine from an aqueous solution to form cephradine crystals, wherein said crystallising is carried out at a temperature of between 45 and 65° C., preferably between 45 and 60° C., preferably between 48 and 55° C. Most preferably, the crystallising is performed at a temperature between 49 and 52° C. Cephradine prepared in an enzymatic process by reacting 7-ADCA with DHa in the presence of an enzyme in a reaction mixture to form cephradine, preferably in a process according to the invention, may advantageously be crystallised at the temperatures disclosed above. However, the temperatures for crystallisation are not limited to crystallisation of cephradine prepared in an enzymatic process, and may for instance advantageously be applied for crystallisation of cephradine prepared in a chemical process (e.g. in the absence of an enzyme).

Cephradine prepared in an enzymatic process by reacting 7-ADCA with DHa in the presence of an enzyme in a reaction mixture to form cephradine, preferably in a process according to the invention, may also be crystallised at a temperature between 35 and 60° C., for instance at a temperature between 35 and 55° C., for instance at a temperature between 35 and 45° C.

Crystallising cephradine from an aqueous solution comprising cephradine may be performed at any suitable pH. Preferably, crystallising the cephradine may be performed at a pH of between 4.0 and 6.0, preferably at a pH of between 4.5 and 5.5, more preferably at a pH of between 4.7 and 5. Surprisingly it was found that at the preferred pH ranges at which crystallisation is performed, the yield of the cephradine crystals was increased. In the framework of the invention, the pH of the aqueous solution may be adjusted in several ways, for instance chemically, by adding an acid, for instance a mineral acid, in particular sulphuric acid, hydrochloric acid or nitric acid. Preferably, said crystallising is performed continuously.

Applying the preferred conditions was surprisingly found to result in cephradine hydrate exhibiting an increased stability in the stability test measured by a decreased absorbance at a wavelength of 450 nm.

The process according to the invention also comprises performing said crystallising at such pH and at such temperature that the absorbance at 450 nm of the cephradine hydrate prepared is below 0.050, preferably below 0.040, and most preferably below 0.030, usually above 0.005.

In one embodiment of the process according to the invention the enzymatic reaction is carried out in the presence of sodium bisulphite. Preferably, the amount of sodium bisulphite present in the enzymatic reaction is between 1 and 25 mM, preferably between 5 and 15 mM. Surprisingly, the presence of sodium bisulphite during the enzymatic reaction further decreased the coloration of the cephradine prepared.

Sodium bisulphite may also be present during crystallisation of cephradine in the process according to the invention. Preferably, the amount of sodium bisulphite present during crystallising of cephradine to form cephradine monhydrate crystals is between 5 and 250 mM, more preferably between 25 and 150 mM.

The cephradine hydrate may be separated from the aqueous solution and dried in any suitable manner.

In another aspect, the invention relates to cephradine hydrate obtainable by the process as described herein. Surprisingly, the coloration of the cephradine hydrate obtainable by the process according to the invention is low, which means that the absorbance at 450 nm is below 0.050, preferably the absorbance at 450 nm is between 0.005 and 0.050, and more preferably of between 0.008 and 0.040, and most preferably between 0.010 and 0.030. It was also found that the cephradine hydrate obtainable by the process according to invention has a high color stability. A high color stability means that low coloration occurs in the stress stability test, i.e. the coloration of the cephradine hydrate is below 0.20, more preferably below 0.15, and most preferably below 0.10 at an absorbance of 450 nm after 8 weeks of storage at 40° C. at a relative humidity of 75%.

In another embodiment, the invention comprises cephradine hydrate with an absorbance at 450 nm of below 0.2, preferably below 0.15, more preferably below 0.1, more preferably below 0.05. Preferably the cephradine hydrate has an absorbance of between 0.001 and 0.2, preferably between 0.002 and 0.15, more preferably between 0.004 and 0.1, more preferably between 0.005 and 0.05, and more preferably of between 0.010 and 0.040. The cephradine hydrate according to the invention has a high color stability in the stress stability test, i.e. the coloration of the cephradine hydrate is below 0.20, more preferably below 0.15, and most preferably below 0.10 at an absorbance of 450 nm after 8 weeks of storage at 40° C. at a relative humidity of 75%.

Preferably, the cephradine hydrate prepared according to the process of the invention contains no, or substantially no dimethylformamide.

The following examples are illustrative for the invention, without limiting the invention thereto.

EXAMPLES

Abbreviations
7-ADCA: 7-aminodesacetoxy cephalosporanic acid
CEF: cephradine
DH: D-dihydrophenylglycine
DHa: D-dihydrophenylglycine in activated form
DHMe D-dihydrophenylglycine methyl ester a) Enzyme and Immobilisation The penicillin acylases as used herein were wild type Pen-G acylase and a Pen-G acylase mutant Phe-24-Ala, as described in WO 98/20120. The enzyme was immobilised as described in EP 222 462 and WO-A-97/04086, with gelatin and chitosan being used as gelling agent and glutaraldehyde as cross-linker.

b) Synthesis of Cephradine

Reference Experiment A.

Synthesis of Cephradine with Assemblase™ (Immobilised Wild-type Pen-G Acylase) at T=20° C. and pH=6.9.

An enzyme reactor, with a sieve bottom with 175 μm gauze was filled with 10 g nett-wet immobilised wild-type Pen-G acylase (enzyme loading 20 mg/g nett-wet biocatalyst). A preparation reactor was filled with 40 ml water (20° C.), 0.03 g sodium bisulphite, 9.15 g 7-ADCA and 9.07 g DHME. The pH was increased to 6.9 with 25% NH$_4$OH solution. Subsequently, the suspension was transferred into the enzyme reactor at t=0 with the aid of 5.0 ml water (T=20° C.). The temperature was kept at T=20° C. The pH was kept at 6.90 with 25% NH$_4$OH solution.

After 300 minutes, [DH]=2.97 mass%, conversion ($n_{CEF}/n_{7-ADCA}$)*100%=68%, conversion ($n_{CEF}/n_{DHa}$)*100%=68% and the S/H=1.8. The reaction mixture became highly viscous due to crystallisation of DH.

Example I

Synthesis of Cephradine with Assemblase™ (Immobilised Wild-type Pen-G acylase) at T=10° C. and pH=7.2→7.5

An enzyme reactor, with a sieve bottom with 175 µm gauze was filled with 92 g nett-wet immobilised wild-type Pen-G acylase (enzyme loading 20 mg/ g nett-wet biocatalyst). A preparation reactor was filled with 190 ml water (10° C.), 1.6 g sodium bisulphite, 36.6 g 7-ADCA (169.8 mmol) and 35.0 g DHME (171.2 mmol). The pH was increased to 7.2 with 25% NH$_4$OH solution. Subsequently, the suspension was transferred into the enzyme reactor at t=0 with the aid of 10.0 ml water (T=10° C.). The temperature was kept at T=10° C. The pH was kept at 7.20 with 25% NH$_4$OH solution during the first part of the reaction. In the second part the pH slowly increased: t=90 min: pH=7.20; t=130 min: pH=7.50.

After 130 minutes, [DH]=0.84 mass%, the conversion ($n_{CEF}/n_{7-ADCA}$)*100%=74%, the conversion ($n_{CEF}/n_{DHa}$)*100%=73% and the S/H=5.5. The initial enzymatic activity is calculated to be ~0.73 µmol CEF/(min·mg enzyme).

Example II

Synthesis of Cephradine with Immobilised Pen-G Acylase Mutant Phe-24-Ala at T=7° C. and pH=8.0→8.2

An enzyme reactor with a sieve bottom with 175 µm gauze was filled with 60.5 g nett-wet immobilised Pen-G acylase mutant Phe-24-Ala (enzyme loading 40 mg/g nett-wet biocatalyst). A preparation reactor was filled with 70 ml water (7° C.), 0.6 g sodium bisulphite, 15.3 g 7-ADCA (71.0 mmol) and 13.9 g DHME (67.7 mmol). The pH was increased to 8.0 with 25% NH$_4$OH solution. Subsequently, the suspension was transferred into the enzyme reactor at t=0 with the aid of 10.0 ml water (T=7° C.). The temperature was kept at T=7° C. The pH slowly increased to 8.20 and was kept at this value with 25% H$_2$SO$_4$.

After 344 minutes, [DH]=0.27 mass%, the conversion ($n_{CEF}/n_{7-ADCA}$)*100%=85%, the conversion ($n_{CEF}/n_{DHa}$)*100%=89% and the S/H=15.5. The initial enzymatic activity is calculated to be ~0.08 µmol CEF/(min·mg enzyme).

Example III

Synthesis of Cefradine with Immobilised Pen-G Acylase Mutant F24A at T=20° C. and pH 6.9

An enzyme reactor with a sieve bottom with 175 µm gauze was filled with 40 g nett-wet immobilised Pen-G acylase mutant Phe-24-Ala (enzyme loading 40 mg/g nett-wet biocatalyst). Then, 110.0 ml water (20° C.), 0.3 g sodium bisulphite, 36.6 g 7-ADCA (169.8 mmol), 1 ml 25% NH$_4$OH solution and 0.04 g EDTA were added. The suspension was stirred for 5 minutes at T=20° C. The pH was 6.90.

In a separate vessel 37.8 g dihydrophenylglycine methylester HCI salt (DHME; 174.7 mmol) was dissolved in 67.2 ml water at T=20° C. From t=0 to t=60 min this solution was dosed into the enzyme reactor with constant dosing rate. The temperature was kept at T=20° C. The pH was kept at 6.90 with 25% NH$_4$OH solution. In the second part of the reaction the pH slowly increased: t=0-240 min: pH=6.90; t=270 min: pH=7.00; t=350 min: pH=7.10.

After 350 minutes, [DH]=0.56 mass%, the conversion ($n_{CEF}/n_{7-ADCA}$)*100%=98.4%, the conversion ($n_{CEF}/n_{DHa}$)*100%=95.6% and the S/H=13.8. The average enzymatic activity from t=0 to 150 min is calculated to be ~0.50 µmol CEF/(min·mg enzyme).

These experiments show that a conversion of 7-ADCA into cephradine higher than 70% and a conversion of DHME into cephradine higher than 70% can be obtained when the DH concentration in the reaction mixture is below 2 wt. %.

TABLE 1

Comparison wild type PenG acylase and mutant PenG acylase Phe-24-Ala at different reaction conditions.

| Reaction conditions Wild type/mutant | Wild type PenG acylase Example I | Mutant PenG acylase Phe-24-Ala Example II |
|---|---|---|
| T = 10/7° C. pH = 7.2-7.8/8.0-8.2 | Conv. 7-ADCA 74% Conv. DHMe 73% S/H: 5.5 [DH] = 0.84% | Conv. 7-ADCA 85% Conv. DHMe 89% S/H: 15.5 [DH] = 0.27% |
| | Ref. Exp. A | Example III |
| T = 20° C. pH = 6.9 | Conv. 7-ADCA 68% Conv. DHMe 68% S/H: 1.8 [DH] = 2.97% | Conv. 7-ADCA 98.4% Conv. DHMe 95.6% S/H 13.8 [DH] = 0.56% |

Conv. 7-ADCA: ($n_{CEF}/n_{7-ADCA}$)*100%
Conv. DHMe: ($n_{CEF}/n_{DHa}$)*100% c) Crystallisation and Isolation of Cephradine.

The reaction mixture obtained as described above was used for crystallisation and isolation. At t=350 minutes (from the start of cephradine synthesis, see above), the mixture comprising the cephradine was cooled to 3° C/ and a suspension of 1.8 g sodium bisulphite in 4.7 ml water was added. Then, the pH was increased to 8.6 with 25% NH$_4$OH solution.

At t=360 minutes, the enzymatic reactor was discharged via the sieve bottom. The (immobilised) enzyme wetcake on the sieve was washed with 2×30 ml water (2° C.). The filtrates and washings were combined and filtrated (successively through filters with pore size 40 µm, 10 µm and 3 µm).

A crystallisation reactor was charged with 3.0 g cephradine and 50 ml water and heated up to T=52° C. Immediately, the combined filtrates and washings were dosed with constant dosing rate in 60 minutes. The temperature was kept at T=52° C. and the pH at 4.80 by titration with 25% sulfuric acid. Then, the temperature was decreased to 25° C. in 30 minutes. The resulting suspension was filtered through a glass filter. The wetcake was washed with 30 ml water and 2×25 ml 80% acetone (acetone/water=80/20 v/v) and dried. 47.0 g cephradine hydrate, with a water content of 3.4%, was obtained.

Reference Experiment B. Chemical Synthesis of Cephradine
1) Mixed Anhydride Preparation A suspension of N-methylacetamide (21.7 grs; 0.30 moles), D(—)α-2,5-dihydrophenylglycine methyl sodium Dane salt (269.9 grs; 0.987 moles), gamma-picoline (0.055 ml; 0.6 mmoles) in dichloromethane (980 ml) was cooled to −20° C., treated with pivaloyl chloride (119.7 grs; 0.991 moles) at −10° C. during 10 minutes, and cooled to −35° C. This system was called preparation A 2) 7-ADCA Solution Dichloromethane (679 ml) was cooled to 50° C. and 7 ADCA (175 grs; 0.817 moles) was loaded. Then diazabicyclo (5,4,0) undec-7-ene (140 grs; 0.920 moles) was added with stirring to obtain complete solution. This system was called preparation B 3) Coupling (Acylation)

Preparation B was added into preparation A, keeping the temperature at −35° C. The resulting reaction mixture C was stirred for 3 hours.

4) Hydrolysis

Water (980 ml) and hydrochloric acid 35% (210 g; 2.0 moles) were added to reaction mixture C and the temperature was brought up to 15° C. The pH was in the range of 1.5 to 2.0. Then, after stirring for 15 minutes, the layers were separated.

5) Vacuum Distillation

The aqueous (upper) layer obtained in step 4 was immediately warmed up to 38° C. and simultaneously distilled under vacuum conditions (initial pressure of about 360 mmHg; final pressure 150 mmHg) to remove the residual dichloromethane. The vacuum distillation was stopped when the GC (gas chromatography) showed a dichloromethane content of 0.7% w/w. A stable (with respect to uncontrolled crystallization of cephradine hydrochloric salt), clear solution, containing cephradine was obtained.

6) Isolation

The obtained solution was warmed up to about 55° C. and cephradine was crystallised by adding triethylamine until pH=5. After filtration, 220 g (0.60 moles; 73% yield) of cephradine (99% assay on dry basis) were obtained. The purity of the thus obtained cephradine was within the specifications of the Chinese Pharmacopeia.

d) Coloration of Cephradine

The coloration of cephradine hydrate was determined by the absorbance at 450 nm. The absorbance and stress stability of the cephradine hydrate prepared as described above were determined.

1. Absorbance 1 g of cephradine hydrate was dissolved in 10 ml 10% aqueous sodium carbonate solution. The absorbance was determined at 450 nm (=$A_{450}$) on a Perkin Elmer 550 S spectrophotometer, with 10% aqueous sodium carbonate solution as a reference solution at room temperature.

2. Stress Stability Test 1.

Cephradine hydrate prepared enzymatically according to Example III and chemically according to Reference Experiment B) was kept at 40° C. at a relative humidity of 75%. After 0, 2, 4, 6 8, 10 and 12 weeks the absorbance at 450 nm was determined as described above.

TABLE 2

Color stability of cephradine hydrate prepared enzymatically and chemically $A_{450}$ and crystallised at 52 and 55° C. at pH 4.8-5.0.

| Weeks | Cephradine prepared enzymatically Crystallisation T = 52° C. | Cephradine prepared chemically Crystallisation T = 55° C. |
|---|---|---|
| 0 | 0.025 | 0.028 |
| 2 | 0.043 | 0.065 |
| 4 | 0.058 | 0.077 |
| 6 |  | 0.161 |
| 8 | 0.096 | 0.142 |

TABLE 2-continued

Color stability of cephradine hydrate prepared enzymatically and chemically $A_{450}$ and crystallised at 52 and 55° C. at pH 4.8-5.0.

| Weeks | Cephradine prepared enzymatically Crystallisation T = 52° C. | Cephradine prepared chemically Crystallisation T = 55° C. |
|---|---|---|
| 10 |  | 0.211 |
| 12 | 0.148 |  |

The results in Table 2 clearly show that the cephradine prepared chemically is less stable with regard to coloration than the cephradine prepared enzymatically.

3. Stress Stability Test 2.

Cephradine hydrate prepared enzymatically according to Example III and crystallised at different temperatures as indicated in Table 3 was maintained during 3 hrs at 100° C. The $A_{450}$ of the cephradine crystals thus treated was determined as described above.

The results in Table 3 clearly show that the crystallization temperature influences the color stability of the cephradine crystals, and that superior values are achieved in experiment V.

TABLE 3

Stability of cephradine hydrate crystals prepared enzymatically and crystallised at different temperatures. The pH during the crystallisation was maintained at 4.80.

| Exp. no° | Crystallisation temperature (° C.) | $A_{450}$ at t = 0 | $A_{450}$ after stress stability test (3 h, 100° C.) |
|---|---|---|---|
| IV | 65 | 0.051 | 0.301 |
| V | 50 | 0.018 | 0.056 |
| VI | 30 | 0.021 | 0.291 |
| VII | 20 | 0.017 | 0.330 |

The invention claimed is:

1. Process for preparing cephradine, said process comprising reacting 7-aminodesacetoxy cephalosporanic acid (7-ADCA) with D-dihydrophenylglycine in activated form (DHa) in the presence of an enzyme in a reaction mixture to form cephradine, resulting in a conversion of 7-ADCA into cephradine of at least 70%, wherein the concentration D-dihydrophenylglycine (DH) in the reaction mixture is below 2 wt. % throughout the reaction;

wherein said enzyme is an acylase having a higher S/H ratio than the wild type acylase of *E.coli* throughout the reacting step and said reacting is carried out at a temperature of at least 15° C.

2. Process according to claim 1, wherein said reacting results in a conversion of 7-ADCA into cephradine of at least 80%.

3. Process according to claim 1, wherein said reacting results in a conversion of D-dihydrophenylglycine in activated form (DHa) into cephradine (CEF) of at least 70%, wherein the conversion of DHa into CEF=$(n_{CEF}/n_{Dha})*100\%$;

$n_{CEF}$=quantity of cephradine formed (in mole); and $n_{Dha}$=total quantity of DHa added to reaction mixture (in mole).

4. Process according to claim 1, wherein the concentration DH in the reaction mixture is maintained below 2 wt. %, throughout said reacting by controlling the pH of the reaction mixture between pH 6 and 9 wherein said reacting is carried out at a temperature of between 15 and 35° C.

5. Process according to claim 1, wherein the sum of the quantity of 7-ADCA added to the reaction mixture and DHa added to the reaction mixture is between 10 and 2000 mmol per liter of reaction mixture.

6. Process according to claim 1, characterized in that dihydrophenylglycine in activated form is dihydrophenylglycine methylester.

7. Process according to claim 1, characterized in that dihydrophenylglycine in activated form is a HCl salt of dihydrophenylglycine methylester.

8. Process according to claim 1, characterized in that the enzyme is immobilized on a carrier.

9. Process according to claim 1, wherein the process is a batch process.

10. Process according to claim 1, wherein said reacting is carried out at a pH of at least 7.0.

11. Process according to claim 1, wherein said reacting is carried out at a pH of below 7.7.

12. Process according to claim 1, characterized in that the enzyme is a mutant penicillin acylase is derived from a wild type acylase via recombinant DNA methodology by substituting one amino acid residue for a new residue.

13. Process according to claim 1, wherein the process comprises crystallizing the cephradine from an aqueous solution to form cephradine hydrate with a water content between 3% and 6% by weight.

14. Process, according to claim 13, said process comprising:
  reacting aminodesacetoxy cephalosporanic acid (7-ADGA) with D-dihydrophenylglycine in activated form (DHa) in the presence of an enzyme in a reaction mixture to form cephradine; and
  crystallizing the cephradine from an aqueous solution, in which aqueous solution the ratio $m_{CEF}/(m_{7\text{-}ADCA}+m_{CEF})>0.7$, preferably $>0.8$, more preferably $>0.9$, and wherein XDH=0-2 wt. %, preferably 0-1 wt. %, wherein
  $m_{CEF}$=molar quantity of cephradine in the aqueous solution;
  $m_{7\text{-}ADCA}$=molar quantity of 7-ADGA in the aqueous solution; and
  $X_{DH}$=concentration of DH in the aqueous solution relative to the total weight of the aqueous solution.

15. Process according to claim 13, wherein the process comprises separating the enzyme from the cephradine prior to said crystallizing.

16. Process according to claim 1, wherein the concentration 7-ADCA in the aqueous solution is between 0 and 5 wt. %.

17. Process according to claim 13, wherein said crystallizing is performed at a temperature of between 45 and 60° C.

18. Process for preparing cephradine hydrate crystals with a water content between 3% and 6% by weight, characterized in that the process comprises crystallizing cephradine from an aqueous solution to form cephradine hydrate, wherein said crystallizing is carried out at a temperature of between 45 and 60° C.

19. Process according to claim 13, wherein said crystallizing is performed at a pH of between 4.0 and 6.0.

20. Process for the preparation of cephradine characterized in that the process comprises:
  reacting 7-aminodesacetoxy cephalosporanic acid (7-ADCA) with D-dihydrophenylglycine in activated form in the presence of an enzyme in a reaction mixture to prepare cephradine; and
  crystallizing the cephradine from an aqueous solution to form cephradine hydrate with a water content between 3% and 6% by weight according to the process according to claim 18.

21. Process according to claim 1, wherein part of the cephradine formed is crystallized and present in the reaction mixture as cephradine hydrate, and wherein the process further comprises dissolving at least part of said cephradine hydrate in said reaction mixture.

22. Process according to claim 21, wherein said dissolving is effected at a pH of above 8.

23. Process according to claim 1 characterized in that said reacting is carried out in the presence of sodium bisulphite.

* * * * *